United States Patent

Deeks

[11] Patent Number: 5,295,963
[45] Date of Patent: Mar. 22, 1994

[54] NEEDLE

[76] Inventor: David J. Deeks, 166 Mt. Eliza Way, Mount Eliza Vic. 3930, Australia

[21] Appl. No.: 603,766
[22] PCT Filed: Apr. 18, 1989
[86] PCT No.: PCT/AU89/00165
 § 371 Date: Nov. 1, 1990
 § 102(e) Date: Nov. 1, 1990
[87] PCT Pub. No.: WO89/10767
 PCT Pub. Date: Nov. 16, 1989

[30] Foreign Application Priority Data

May 6, 1988 [AU] Australia ............................. PI8108
Jul. 1, 1988 [AU] Australia ............................. PI9109

[51] Int. Cl.⁵ .............................................. A61M 5/32
[52] U.S. Cl. ................................. 604/110; 604/198; 604/263
[58] Field of Search ............... 604/110, 187, 198, 263, 604/192

[56] References Cited

U.S. PATENT DOCUMENTS

| | | |
|---|---|---|
| 2,674,246 | 4/1954 | Bower . |
| 2,876,770 | 3/1959 | White . |
| 3,134,380 | 5/1964 | Armao . |
| 3,306,290 | 2/1967 | Weltman . |
| 4,564,054 | 1/1986 | Gustavsson . |
| 4,664,654 | 5/1987 | Strauss . |
| 4,725,267 | 2/1988 | Vaillancourt . |
| 4,767,413 | 8/1988 | Haber et al. . |
| 4,775,369 | 10/1988 | Schwartz . |
| 4,795,432 | 1/1989 | Karczmer .......................... 604/110 |
| 4,804,371 | 2/1989 | Vaillancourt ...................... 604/198 |
| 4,813,940 | 3/1989 | Parry ................................... 604/198 |

FOREIGN PATENT DOCUMENTS

63661/73 12/1972 Australia .

Primary Examiner—John D. Yasko
Attorney, Agent, or Firm—Larson and Taylor

[57] ABSTRACT

A needle assembly is disclosed which comprises a hub (12) to which a needle (20) is fixed. A spring (30) is coupled to the hub (12) and surrounds the needle (20). The free end of the spring (30) retains an end cap (32) which is intended to cover the tip of the needle (20) after use of the needle assembly. A clamp (34) may be used to maintain the spring (30) compressed so that the needle assembly can be used and after use the clamp (34) is removed so that the needle biases the end cap (32) into a position where it covers the end of the needle (20). Alternatively, a deformable cylinder (80) may be coupled with the hub (12) and have clip members (82) which engage corresponding clip recess (84) on the end cap (32) to maintain the spring (30) compressed. Upon deformation of the deformable member (80) the end cap (32) is released from the deformable member (80) so that the spring (30) biases the end cap (32) into a position encapsulating the end of the needle.

9 Claims, 2 Drawing Sheets

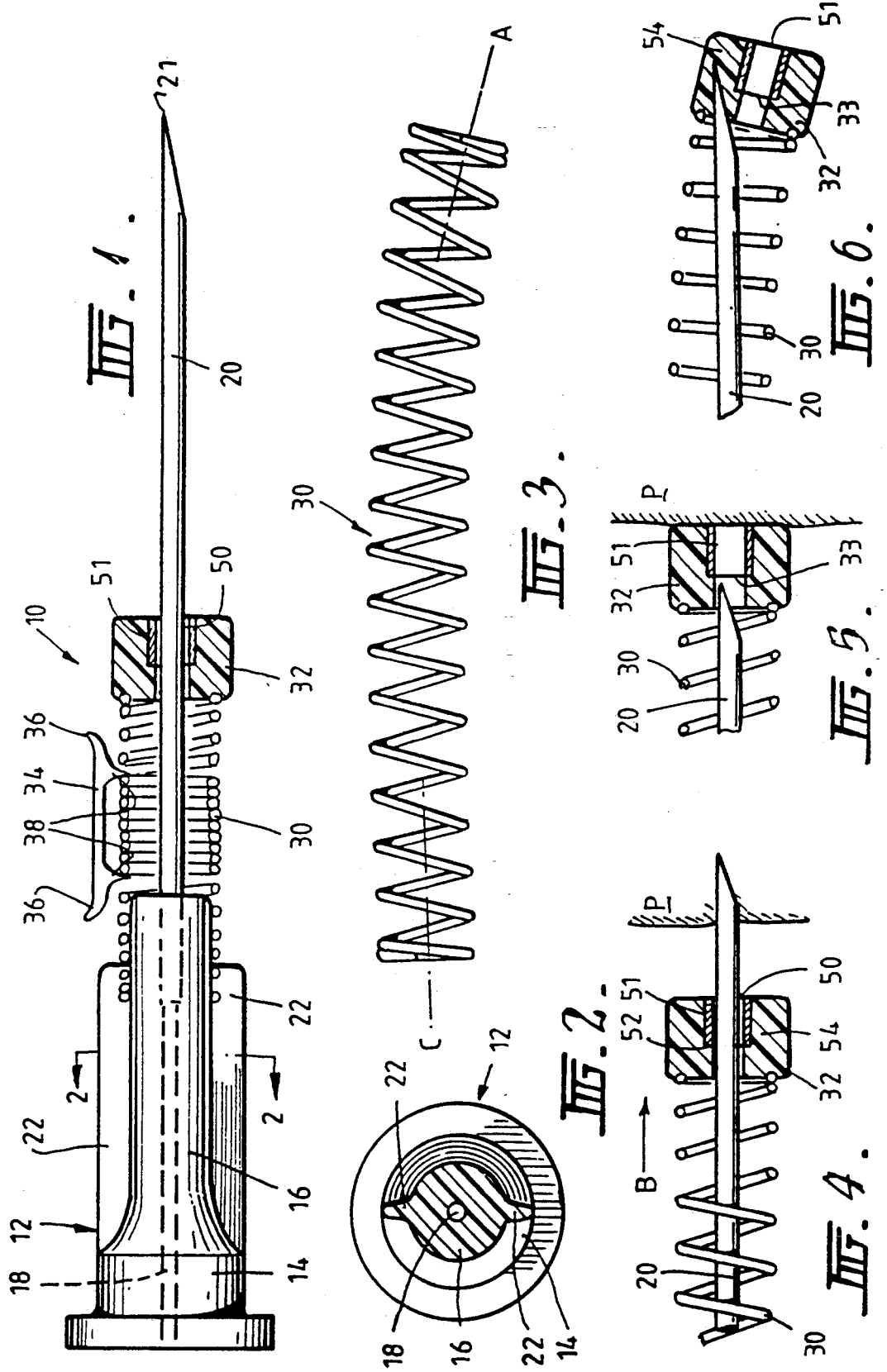

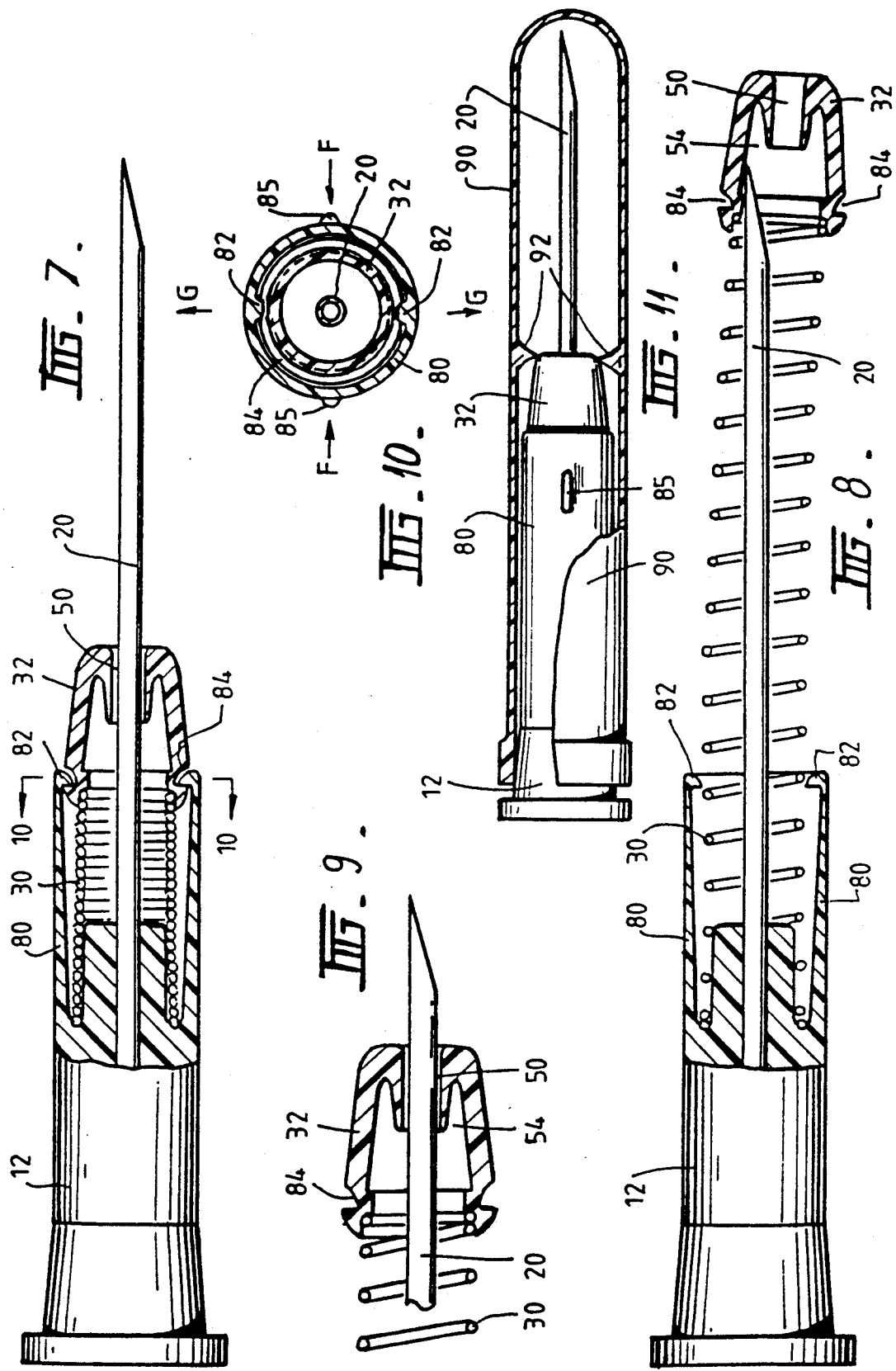

NEEDLE

BACKGROUND OF THE INVENTION

This invention relates to a needle and in particular to a hypodermic needle, acupuncture needle or other needle which is intended to puncture the skin of a person or animal.

Such needles and, in particular, hypodermic needles which are intended to administer medicine or take blood samples may become contaminated if the patient or animal is suffering from a disease such as AIDS, hepatitis or the like. Although these needles are usually used by trained medical staff there is always a possibility that a person can puncture himself or herself whilst holding the syringe supporting the needle or by dropping the syringe thereby puncturing a leg or foot. If the needle is contaminated, it is possible that the accidental puncturing of a person will transmit the disease to that person.

The object of this invention is to provide a needle and a device to prevent accidental puncturing by a needle which overcome these problems.

SUMMARY OF THE INVENTION

The invention, in a first aspect, may be said to reside in a needle, said needle having a cover member for covering a point of the needle and biasing means for biasing said covering means into a position wherein the point of the needle is covered by the covering means.

The invention, in a second aspect, may be said to reside in a device to prevent accidental puncturing by a needle, said device comprising a cover member and biasing means for biasing said cover member into a position wherein a point of said needle is covered by said cover member.

Since the point of the needle has a cover means biased into a position wherein the point of the needle is covered by the cover member, if the needle is dropped or pressed against a person, the cover member will prevent the needle from puncturing the person's skin thereby preventing the transmission of diseases.

Preferably, said cover member is in a first position remote from the point of the needle prior to use of the needle and after the needle has been used, said biasing means biases said cover member into a position wherein the point of the needle is covered.

Preferably, the cover member, when biased into a position covering the point of a needle, prevents access to the point of the needle thereby ensuring that a contaminated needle cannot puncture a person's skin.

Preferably said biasing means is curved and the end cap has an aperture through which the needle can project, said biasing means biasing said end cap into a position where the point of the needle is covered by said end cap and is within the confines of the end cap, the curved biasing means causing said end cap to be moved transversely with respect to said needle so that the needle is not aligned with said aperture.

In one embodiment of the invention, a clamp is used to maintain the spring in a compressed state prior to use of the needle. In a second and preferred embodiment, the spring is maintained compressed by a deformable member which engages the cap and holds the cap inwardly of the end of the needle to, in turn, hold the spring compressed. The deformable member is deformed so that it releases the cap so that, in turn, the spring can bias the cap to the end of the needle so that it covers the end of the needle.

BRIEF DESCRIPTION OF THE DRAWINGS

A preferred embodiment of the invention will be described in more detail with reference to the accompanying drawings in which:

FIG. 1 is a side view of a needle and the device embodying the invention;

FIG. 2 is a view along the line 2—2 of FIG. 1;

FIG. 3 is a view of a spring used in the embodiment of FIG. 1;

FIG. 4 is a view of the needle in use;

FIG. 5 is a view of the needle immediately after withdrawal from a patient;

FIG. 6 is a view of the needle after use;

FIG. 7 is a view of a second embodiment;

FIG. 8 is a view of the embodiment of FIG. 7 in the after use condition;

FIG. 9 is an enlarged view of part of the embodiment of FIG. 7;

FIG. 10 is a cross-section view along the line 10—10 of FIG. 7; and

FIG. 11 is a side view similar to FIG. 7 incorporating a protector.

DETAILED DESCRIPTION OF THE PREFERRED EMBODIMENT

With reference to the accompanying drawings, the preferred embodiment of the invention will be described with reference to a hypodermic needle. However, it should be understood that the invention could be used with other types of needles.

A hypodermic needle 10 is shown which has a hub 12. The hub 12 is intended to be located on a syringe (not shown) by friction fit or in any other suitable means. The hub 12 has an enlarged diameter portion 14 and a reduced diameter portion 16. A bore 18 extends through the hub 12 to a needle 20 which projects outwardly of the hub.

In order to strengthen the hub 12, the hub 12 includes ribs 22.

A spring 30 is arranged over the needle 20 and is secured to the hub 12 preferably by adhesive or moulding the spring 30 into the hub 12 which is preferably formed from plastics material. The free end of the spring 30 carries an end cap 32 which may be formed from plastics material or stainless steel. The spring 30 is preferably formed from stainless steel but could be made from plastics material.

The length of the spring 30 when in a compressed state is such that the cap 32 is arranged inwardly of the point 21 of the needle 20 and in the fully extended position biases the cap 32 to a position wherein the point 21 of the needle is within the confines of the cap 2 and between the inner end 31 of the cap and the end 33 of a bore 50 in the cap 32 (as is best seen in FIG. 5).

A clamp 34 is provided to retain at least part of the spring 30 in the compressed position so that the end cap 32 is inwardly of the point 21 of the needle 20. The clamp 34 is preferably formed from a resilient plastics material so that tabs 36 can be engaged by a user's fingers and the clamp 34 flexed so that it disengages from the spring 30 to enable the spring 30 to bias the end cap 32 towards the point 21 of the needle 20. In order to accommodate the clamp 34 the spring 30 may have coils which are of such a pitch that engaging tabs 38 of the clamp 34 are insertable between coils of the spring 30 to hold a portion of the spring 30 in the compressed condition.

The spring 30, as best seen in FIG. 3, is curved symmetrically or at one end. The spring 30 can be curved by heat treatment, or have the curve induced with memory in plastic material, or any other suitable method. Central axis C of the spring 30 is not aligned with the central axis A of the end of the spring 30 to which the end cap 32 is connected. The end cap 32 is preferably coupled to the spring 30 by welding the spring 30 to the end cap or adhering the spring 30 to the end cap or by any other suitable means. The end cap 32 has an aperture 51 communicating with a central bore 50 and aperture 51 which enables the needle 20 to pass through the end cap. The bore 50 is defined by a sleeve 52 connected to or formed integral with the cap 32 and aligned with the aperture 51. The sleeve 52 defines with the remainder of the end cap 32, an annular housing portion 54. The bore 50 and aperture 51 are slightly larger than the diameter of the needle 20 so that the end cap 32 can comfortably move relative to the needle 20.

Prior to use, the needle is retained in the position shown in FIG. 1 wherein the spring 30 is compressed and the end cap 32 is arranged inwardly of the end of the tip 21. Prior to use, the needle 10 may be maintained in a sterile container, bag or the like. In order to use the needle, the needle is attached to a syringe and the tip of the needle 21 is inserted into a patient or animal. The contents of the syringe may then be injected into the patient or animal or blood may be withdrawn from the patient or animal. Prior to removing the needle from the patient or animal the clamp 34 is removed from the spring 30 by engaging the portions 36 and flexing the clamp 34 so that the tabs 38 are released from the spring 30. When the clamp 34 is released from the spring 30, the spring biases the end cap 32 towards the point 21 in the direction of arrow B until the end cap 32 engages the patient's skin. The needle may then be withdrawn from the patient P. As the needle is withdrawn from the patient the spring 30 continues to bias the end cap 32 towards the tip 21 of the needle thereby generally maintaining the end cap 32 in engagement with the patient P. Thus, when the needle is removed from the patient's skin, the end cap 32 is biased by the spring 30 over the tip 21 and into the position shown in FIG. 5.

In view of the curved nature of the spring 30 the spring, when in fully extended position, after the tip 21 of the needle has left the bore 50, moves the end cap transversely relative to the needle so that the needle 20 is no longer aligned with the bore 50 and aperture 51 in the end cap 30 but is accommodated in the end cap 32 generally in the housing portion 54 as is best seen in FIG. 6.

Since the tip 21 of the needle 20 is accommodated within the end cap 32 and is misaligned with the bore 50 and aperture 51 the needle cannot accidentally puncture a person's skin if it is accidentally brought into contact with a person or is dropped. In view of the relatively small size of the bore 50 and aperture 51 compared to the end cap 32 the needle is unlikely to accidentally re-engage with the bore 50 and therefore cannot escape from the confines of the end cap 52. Thus, the tip 21 of the needle is safely and immediately automatically covered by the end cap after the needle is withdrawn from a patient or animal.

After use, the needle 10 may be sterilized or disposed of.

A second embodiment of the invention is shown in FIGS. 7 to 11. In this embodiment (in which like reference numerals designate like parts) the hub 12 is provided with a deformable extension 80 which is preferably cylindrical in nature as shown in the drawings or which can comprise two or more semi-cylindrical members or rail-like members which extend generally parallel to the needle 20. As is best shown in FIGS. 8 and 10, the member 80 has a first component of an interengaging clip which engages second components of the clip which are arranged on the end cap 32 (which, in this embodiment, is rounded rather than square as in the earlier embodiment). The first component of the clip may comprise a pair of diametrically opposite projections which project inwardly of the member 80 and the second components of the clip may comprise a circular recess around the whole of the outside of the cap opposite recesses 84 formed in the outer side wall portion of the end cap 32 to engage the projections 82 (as shown in FIGS. 7 and 11).

In this embodiment of the invention the spring 30 is the same as that used in the previous embodiment and may be moulded into the hub 12 or fixed by adhesive, clips or the like. The opposite end of the spring may be retained on the inner surface of the cap 32 by any suitable means including retaining lugs, adhesive or by being moulded in to the end cap. The spring 30 is compressed so that the interengaging recesses and projections 82 and 84 may engage one another so that the end cap 32 is retained in place at the end of the member 80 and the spring is therefore maintained in the compressed state.

The deformable member 80 is provided with pips or protrusions 85 arranged 90° out of phase with the projections 82 and recess 84 as is shown in FIG. 10.

After the needle has been used and it is desired to release the end cap 32 so that the end cap is biased to the end of the needle to take up the position shown in FIG. 8 where it is located generally within annular housing portion 54, the operator merely locates lugs 85 with his or her fingers and squeezes the lugs inwardly in the direction of arrow F. When the lugs 85 are squeezed the adjacent portions of the deformable member 80 are forced inwardly in the direction of arrows F so that the end of the deformable member 80 forms an oval shape with the top and bottom of member 80 flexing outwardly in the direction of arrows G so that the recesses 82 are disengaged from the projection 84 to thereby release the end cap 32. As noted above, the end cap is then bias by the spring 30 to the end of the needle 20.

In this embodiment of the invention a tubular protector 90 (FIG. 11) may be provided which is located over the needle 20, spring 30 and deformable member 80 and friction held to hub 12 to protect the needle during storage or in transportation. The earlier embodiment may include a similar protector. The protector 90 may have retaining lugs 92 for holding the end cap 32 in place in the event that the projections 82 and the recesses 84 of the clip become disengaged during transportation.

As in the earlier embodiment, the spring 30 is preferably curved so that when the end cap 32 is biased to the end of the needle 20 the tip of the needle is not aligned with the bore 50 as described with reference to the first embodiment.

In other embodiments (not shown) a straight spring could be used with its axis angled on attachment to the hub 12 and the bore 50 could be non-centrally aligned so that when the end cap 32 is biased over the end of the needle 20 the needle will not be aligned with the bore 50. Furthermore, a straight spring could be used with the end cap being angled so as to misalign the needle 20 with the bore 50 when the end cap is forced over the needle 20. Furthermore, the spring could be offset or twisted so that the non-centrally aligned bore 50 is not aligned with the needle 20 after use. In other embodiments it would also be possible to arrange the spring 30 so that it is outwardly of the end cap 32 rather than retained within the end cap 32.

Since modification within the spirit and scope of the invention may readily be effected by persons skilled within the art, it is to be understood that this invention is not limited to the particular embodiment described by way of example hereinabove.

I claim:

1. A needle assembly comprising:
   a hub for connection to a syringe;
   a needle connected to said hub and extending outwardly from said hub, said needle having a pointed end;
   a spring having a first end secured to said hub and a second end;
   an end cap secured to the second end of said spring, said end cap having an aperture so that the needle can pass through said aperture and said end cap can move along said needle relative to the needle;
   a first engagement member on said end cap;
   at least one deformable member coupled to said hub;
   a second engagement member on said deformable member for releasable engagement with said first engagement member;
   wherein said end cap is retained inwardly of said pointed end on said needle by engagement of the first engagement member with said second engagement member and with the needle projecting through said aperture and said spring being compressed, and wherein said deformable member is deformable by finger pressure so that the first and second engagement members are releasable from one another so that said spring biases said end cap to the pointed end of the needle so that the end cap covers said pointed end, said spring mechanically forcing said end cap to a position wherein the needle and the aperture in the end cap are not aligned with one another so that the needle cannot accidentally pass back through said aperture.

2. The needle assembly according to claim 1 wherein said end cap has a annular housing portion which accommodates said pointed end of the needle when the end cap is mechanically forced into the position wherein the end point is covered by the end cap and the needle and aperture in the end are not aligned.

3. A needle assembly comprising:
   a hub for connection to a syringe;
   a needle connected to said hub and extending outwardly from said hub, said needle having a pointed end;
   a spring having a first end secured to said hub and a second end;
   an end cap secured to the second end of said spring, said end cap having an aperture so that the needle can pass through said aperture and said end cap can move along said needle relative to the needle;
   a first engagement member on said end cap;
   at least one deformable member coupled to said hub;
   a second engagement member on said deformable member for releasable engagement with said first engagement member;
   wherein said end cap is retained inwardly of said pointed end on said needle by engagement of the first engagement member with said second engagement member and with the needle projecting through said aperture and said spring being compressed, and wherein said deformable member is deformable by finger pressure so that the first and second engagement members are releasable from one another so that said spring biases said end cap to the pointed end of the needle so that the end cap covers said pointed end, said spring mechanically forcing said end cap to a position wherein the needle and the aperture in the end cap are not aligned with one another so that the needle cannot accidentally pass back through said aperture, the deformable member comprising a cylindrical member formed integral with said hub and surrounding said needle and spring, said first and second engagement members comprising at least one projection on one of said cylindrical member and said end cap and at least one recess on the other of said cylindrical member and end cap, said at least one projection being receivable in said at least one recess to couple the end cap to the cylindrical member to maintain said spring in the compressed state and wherein finger pressure on said cylindrical member deforms said cylindrical member into an oval shape so that said at least one projection is moved out of said at least one recess to enable said spring to bias said end cap to the pointed end of the needle.

4. The needle assembly according to claim 3 wherein said end cap has an annular housing portion which accommodates said pointed end of the needle when the end cap is mechanically forced into the position wherein the end point is covered by the end cap and the needle aperture in the end cap are not aligned.

5. The needle assembly according to claim 3 wherein said cylindrical member includes at least one finger location member which defines a position at which finger pressure can be applied to deform the cylindrical member so as to release said at least one projection from said at least one recess.

6. A needle assembly comprising:
   a hub for connection to a syringe;
   a needle connected to said hub and extending outwardly from said hub, said needle having a pointed end;
   a spring having a first end secured to said hub and a second end;
   an end cap secured to the second end of said spring, said end cap having an aperture so that the needle can pass through said aperture and said end cap can move along said needle relative to the needle;
   a first engagement member on said end cap;
   at least one deformable member coupled to said hub;
   a second engagement member on said deformable member for releasable engagement with said first engagement member;
   wherein said end cap is retained inwardly of said pointed end on said needle by engagement of the first engagement member with said second engagement member and with the needle projecting through said aperture and said spring being compressed, and wherein said deformable member is deformable by finger pressure so that the first and second engagement members are releasable from one another so that said spring biases said end cap to that pointed end of the needle so that the end cap covers said pointed end, said spring mechanically forcing said end cap to a position wherein the needle and the aperture in the end cap are not aligned with one another so that the needle cannot accidentally pass back through said aperture, said spring being a curved spring curved relative to the needle so that curvature of the spring mechanically forces the end cap into the position where the needle and aperture in the end cap are not aligned.

7. The needle assembly according to claim 6 wherein said end cap has an annular housing portion which accommodates said pointed end of the needle when the end cap is mechanically forced into the position wherein the end point is covered by the end cap and the needle aperture in the end cap are not aligned.

8. A needle assembly comprising:
 a hub for connection to a syringe;
 a needle connected to said hub and extending outwardly from said hub, said needle having a pointed end;
 a spring having a first end secured to said hub and a second end;
 an end cap secured to the second end of said spring, said end cap having an aperture so that the needle can pass through said aperture and said end cap can move along said needle relative to the needle;
 a first engagement member on said end cap;
 at least one deformable member coupled to said hub;
 a second engagement member on said deformable member for releasable engagement with said first engagement member;
 wherein said end cap is retained inwardly of said pointed end on said needle by engagement of the first engagement member with said second engagement member and with the needle projecting through said aperture and said spring being compressed, and wherein said deformable member is deformable by finger pressure so that the first and second engagement members are releasable from one another so that said spring biases said end cap to the pointed end of the needle so that the end cap covers said pointed end, said spring mechanically forcing said end cap to a position wherein the needle and the aperture in the end cap are not aligned with one another so that the needle cannot accidentally pass back through said aperture, said spring being straight and said end cap being angled relative to the spring so that when the spring biases the end cap to the pointed end of the needle the spring mechanically forces the end cap into a position where, by virtue of the angular relation between the straight spring and end cap, the aperture in the end cap is not aligned with the needle.

9. The needle assembly according to claim 8 wherein said end cap has an annular housing portion which accommodates said pointed end of the needle when the end cap is mechanically forced into the position wherein the end point is covered by the end cap and the needle aperture in the end cap are not aligned.

* * * * *